United States Patent [19]

Rönka et al.

[11] Patent Number: 4,636,477

[45] Date of Patent: Jan. 13, 1987

[54] PROCEDURE FOR LOADING CUVETTE PACKAGES INTO AN INSTRUMENT, AND CUVETTE PACKAGE

[75] Inventors: Pekka Rönka; Raimo Vaintola, both of Espoo, Finland

[73] Assignee: Kone Oy, Helsinki, Finland

[21] Appl. No.: 699,572

[22] Filed: Dec. 28, 1984

[30] Foreign Application Priority Data

Dec. 30, 1983 [FI] Finland ................................. 834882

[51] Int. Cl.$^4$ ......................... G01N 35/02; B01L 3/14
[52] U.S. Cl. ..................................... 436/48; 436/809; 422/66; 422/102; 206/216; 206/569; 414/417
[58] Field of Search ................... 422/66, 102; 436/47, 436/48, 164, 809; 356/240, 440; 414/181, 417; 206/216, 569

[56] References Cited

U.S. PATENT DOCUMENTS

| | | | |
|---|---|---|---|
| 4,198,484 | 4/1980 | Reichler et al. | 422/102 |
| 4,292,273 | 9/1981 | Butz et al. | 422/102 |
| 4,319,841 | 3/1982 | Suovaniemi et al. | 422/102 |
| 4,357,301 | 11/1982 | Cassaday et al. | 422/102 |
| 4,389,374 | 6/1983 | Sutton et al. | 422/102 |

Primary Examiner—David L. Lacey
Attorney, Agent, or Firm—Browdy and Neimark

[57] ABSTRACT

A procedure for loading into an instrument cuvettes intended for chemical analysis and/or handling of liquids, said cuvettes being loaded into the instrument directly from the shipping package, and a cuvette package. The cuvette package includes a box portion for supporting the cuvettes having an open feeding end, and a cover portion detachable from the box portion and provided with a depending pushing member. When the cover portion is disposed contiguously atop the box portion to form the package, the pushing member closes the feeding end to securely contain any cuvettes therein. When the cover portion is detached from the box portion, dust-free and scratch-free transfer of cuvettes into the instrument while the package is attached to an input aperture of the instrument may be accomplished by pushing, from behind, the rows of cuvettes in the package with the pushing member of the cover portion.

9 Claims, 6 Drawing Figures

PROCEDURE FOR LOADING CUVETTE PACKAGES INTO AN INSTRUMENT, AND CUVETTE PACKAGE

BACKGROUND OF THE INVENTION

The present invention concerns a cuvette package, and a method for loading an instrument intended for chemical analysis and/or handling of liquids with cuvettes from the package, said cuvettes being loaded into the instrument directly from a shipping package.

For the purpose of analyzing various liquids, automatic analyzers are used in laboratories in which the liquids to be analyzed are located in so-called reaction vessels, which at the same time serve as cuvettes of good optical quality. A row of reaction vessels, or a cuvette, may usually be composed of a plurality of reaction vessels mutually separated by a wall and which have been cast in the form of an integral row. A cuvette of this type is disclosed in the Finnish patent application No. 820372. Cuvettes like this are simple to handle, and reliable results of measurement are obtained with their aid.

The cuvettes should stay dust-free, free of scratches and intact so that the radiant flux, which in the instrument performing the analysis is caused to pass through the measuring surfaces of the reaction vessels, might yield reliable results of analysis. The cuvettes must for this reason be handled with great caution immediately after the manufacturing step and during packaging, storage, transport and use.

In the course of using such cuvettes, the need has arisen to devise a cuvette loading procedure which would guarantee that the cuvettes, when taken into use, are absolutely dust-free, free of scratches and free of fingerprints. The packaging step following the step in which the cuvettes are die-cast can be managed by methods and equipment of automation technology, whereas impacts acting on the cuvette packages proper, and human handling errors when the cuvettes are being loaded into the instrument performing the analysis, have constituted problems.

SUMMARY OF INVENTION

In order to minimize these problems, the procedure of the invention is mainly characterized in that cuvettes are transferred into the instrument while the package is attached to the input aperture of the instrument. This is accomplished by pushing from behind the row of cuvettes which is in the package from behind with the detachable cover of the package, which is provided with a separate pushing member. When the cover is attached to the package the pushing member forms one end of the package.

The advantages of the procedure of the invention are: dust-free handling, no fingerprints in the optical area, and no scratches from manual handling.

The procedure of the present invention is characterized in that the cuvettes are moved in the package by point or line contact, established by projections carried on the pushing member, between the pushing member and the cuvette nearest to it. These projections are directed against the partitions between the different reaction vessels in said cuvette, or against its margin.

Projections thus placed enable the cuvette to be pushed into the instrument free of scratches and they render possible pushing or pulling the cuvettes which remain unused back into the package.

The procedure of the present invention is further characterized in that when the transferring of cuvettes into the instrument has come to an end, if there are still cuvettes remaining in the package, the last cuvette on the feeding end of the package, which has been specifically shaped to this purpose, remains in its place, preventing the falling out of cuvettes and enabling them to be pushed back with the pushing member on the cover. It is thus easy to handle a partly emptied package, since the cuvettes will not fall out.

The cuvette package of the invention is characterized in that the cover forms a detachable cuvette transferring tool with which the cuvettes can be transferred into any desired instrument while the package is attached to the instrument's input aperture, and that a separate pushing member for moving the cuvettes is provided on the cover of the package, which when the cover is attached to the package forms one end of the package.

One advantageous aspect of the cuvette package of the invention is that the pushing member on the cover is provided with projections which serve as contact points between the pushing member and the nearest cuvette and which are directed against the partitions between the cuvette's different reaction vessels or against its margin.

Another advantageous aspect of the cuvette package of the invention is that the cover of the package is detachable and reattachable with a vertical movement, and that when it is used as transferring tool it can be moved, pressed contiguous with the package, in the longitudinal direction of the package. The cover part is held contiguous with the package through the shape which has been given to the sides of the cover, yet it is possible to lift it off with minor force. Since all steps can be implemented as movements along perpendicular paths, it is easy, for instance, to automate the loading process.

Yet another advantageous aspect of the cuvette package of the invention is that the package is made of shock-resistant polystyrene.

BRIEF DESCRIPTION OF THE DRAWING

The invention is more closely described with the aid of an example, reference being made to the attached drawing, wherein.

DETAILED DESCRIPTION OF PREFERRED EMBODIMENT

Figure 1:
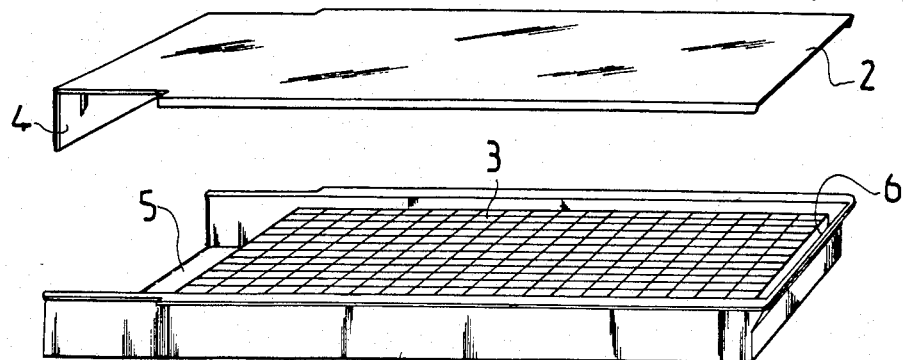
FIG. 1 depicts in perspective a full cuvette package, showing its cover detached.

In FIG. 1 is depicted a package according to the invention, which permits dust-free and scratch-free storage and use of the cuvettes. The package consists of a box part 1 and a cover part 2. The package is filled with cuvettes 3 right at the place where they are manufactured. Other features of the package are: the pushing member 4, belonging to the cover at one end, the forward feeding end 5 of the box part and the chamfer 6 on its other end, i.e., in the rear end, which facilitates the insertion of the pushing member 4 behind the line of cuvettes.

Figure 2:
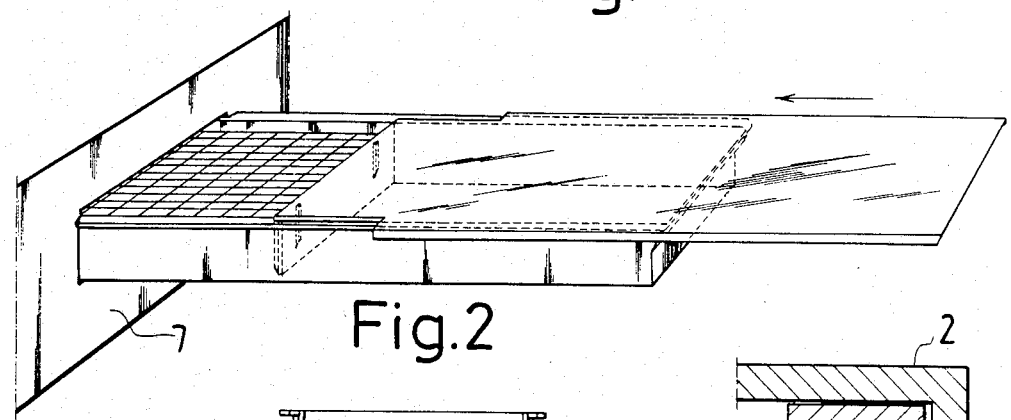
FIG. 2 shows the cuvette package in a loading position as viewed obliquely from above.

In FIG. 2 is illustrated the emptying of the package e.g. into an automatic analyzer 7: the cover 2 is detached, the feeding end 5 of the box part 1 is pushed into the analyzer 7, whereby the package will be held there without anybody holding it, the pushing member 4 is inserted behind the row of cuvettes with the aid of the chamfer 6, and the cuvettes are pushed forwardly into the analyzer as indicated by the arrow.

Figure 3:
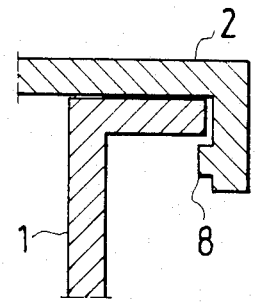
FIG. 3 shows in cross-section the juncture between the package and the cover.

FIG. 3 shows how the cover part 2 keeps contiguous with the box part 1 by reason of its sides. The cover snaps fast to the lower part, thanks to the borders 8. However, the shaping of the borders 8 together with the choice of material for the package guarantees that the cover part 2 can be detached from the box part 1 by lifting it straight up.

Figure 4A:
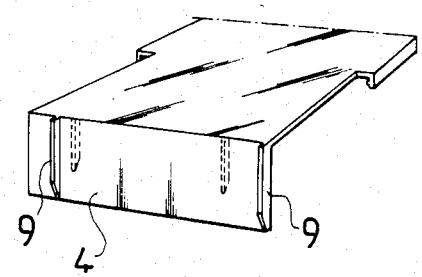
FIGS. 4a and 4b show the pushing member on the cover.
Figure 4B:
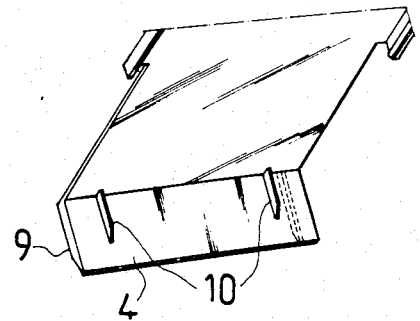

FIGS. 4a and 4b illustrate how there are eminences, or projections, 9 and 10 on both sides of the pushing member 4, which prevent the optical faces of the cuvettes from being scratched even if the row of cuvettes should be treated carelessly in its package. The projections 9 meet the surfaces between reaction vessels in the rearmost cuvette, or its margin, when the rows 3 are being pushed into the instrument 7, and the projections 10 operate similarly during storage of the cuvettes and when they are possibly pulled back from the feeding end 5 of the box part into the package. On the other end of the package, below the chamfer 6, projections 11 have also been provided (FIG. 5), which during storage prevent the faces of the cuvettes from rubbing against the box part rear end.

Figure 5:
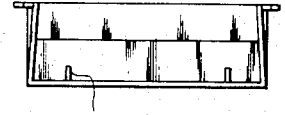
FIG. 5 shows the feeding end of the cuvette package, in front view.

FIG. 5 shows how the feeding end 5 of the package has on its sides been shaped to be tapering upward from below, so that the first cuvette that remains in the package will be held in the package by the pressure exerted by the sides. In this way the use is made easier, since the cuvettes cannot fall out through the end of the coverless package.

It is obvious to a person skilled in the art that different embodiments of the invention are not exclusively confined to the example presented above and that they may vary within the scope of the claims stated below.

We claim:

1. A procedure for loading into an instrument cuvettes intended for chemical analysis and/or handling of liquids, said cuvettes being arranged in at least one row in a shipping package having a detachable cover and being loaded in a forward direction into an input aperture of the instrument directly from the shipping package, comprising:

transferring the cuvettes into the instrument by pushing the cuvettes in the package from behind with the detachable cover of the package, the cover being provided with a separate pushing member which, when the cover is contiguous with the package, forms one end of the package.

2. The procedure according to claim 1, and further comprising:

providing projections on the pushing member, and moving the cuvettes in the package with point or line contact by interposition of said projections provided on the pushing member behind the cuvette adjacent to the pushing member, said projections being directed against partitions between different reaction vessels in said cuvette.

3. The procedure according to claim 1, wherein the package has a forward end, and opposite rear end and sides, the forward end being narrower than the rear end, whereby cuvettes in the forward end are compressed against the sides of the package thereby holding the cuvettes in place unless pushed by the pushing member, and further comprising:

halting the transferring of the cuvettes into the instrument before all of the cuvettes in the package have been transferred into the instrument, and moving the remaining cuvettes rearwardly back into the package with the pushing member on the cover.

4. A cuvette package adapted for feeding liquid-containing cuvettes to be carried in the package into an instrument for chemically analyzing and/or handling the contained liquid, the package comprising:

a box portion for supporting the cuvettes and having a bottom, upstanding opposing sides, an upstanding front end and an open feeding end, and a cover portion placed atop, and detachable from, the upstanding opposing sides of said box portion, said cover portion including a top, sides, and an end having a downwardly depending pushing member which closes the feeding end of the box portion to securely house the cuvettes to be contained therein, said detachable cover portion and pushing member defining a tool for pushing the cuvettes into an instrument when said cover is detached and said package is attached to an input aperture of the instrument.

5. A cuvette package according to claim 4, wherein said pushing member includes projections which serve as contact points between the pushing member and a cuvette closest thereto.

6. A cuvette package according to claim 4, wherein the sides of the cover portion and the box portion include complementarily configured means for vertically detaching and reattaching said cover portion and said box portion, said complementarily configured means coacting to press said cover portion to said box portion and to permit longitudinal sliding movement of said cover portion relative to said box portion when said cover portion and pushing member are used as said tool.

7. A cuvette package according to claim 4, wherein the sides at the feeding end of said box portion are narrower than the sides at the front end whereby the cuvettes are compressed against the sides of the package at the feeding end so that a cuvette that has been left at the feeding end remains in place without falling out of the package.

8. A cuvette package according to claim 4, wherein the package is made of shock-resistant polystyrene.

9. The cuvette package of claim 4, wherein said box portion front end includes chamfered means for facilitating insertion of the pushing member into the box portion forwardly of the cuvettes so that the cuvettes can be pushed into the instrument from said box portion.

* * * * *